United States Patent [19]

Kobayashi

[11] Patent Number: 5,353,073
[45] Date of Patent: Oct. 4, 1994

[54] THREE-DIMENSIONAL SHAPE MEASUREMENT SYSTEM

[75] Inventor: Koji Kobayashi, Hino, Japan

[73] Assignee: Kowa Company, Ltd., Japan

[21] Appl. No.: 945,672

[22] Filed: Sep. 16, 1992

[30] Foreign Application Priority Data

Sep. 17, 1991 [JP] Japan .................................. 3-235239

[51] Int. Cl.⁵ .......................... A61B 3/10; G01B 11/24
[52] U.S. Cl. ..................................... 351/221; 356/376
[58] Field of Search ................ 351/206, 221; 356/376; 250/560

[56] References Cited

U.S. PATENT DOCUMENTS

| | | | |
|---|---|---|---|
| 4,755,047 | 7/1988 | Kato et al. | 356/376 |
| 4,764,005 | 8/1988 | Webb et al. | 351/221 |
| 4,802,759 | 2/1989 | Matsumoto et al. | 356/376 |
| 4,854,692 | 8/1989 | Kobayashi | 351/206 |
| 4,900,144 | 2/1990 | Kobayashi | 351/206 |
| 5,033,856 | 7/1991 | Nose et al. | 356/376 |
| 5,074,307 | 12/1991 | Aizu et al. | 351/206 |
| 5,088,811 | 2/1992 | Hideshima et al. | 351/221 |
| 5,104,227 | 4/1992 | Uesugi | 356/376 |
| 5,129,400 | 7/1992 | Makino et al. | 351/206 |
| 5,152,295 | 10/1992 | Kobayashi et al. | 351/206 |
| 5,177,511 | 1/1993 | Feuerstein et al. | 351/221 |
| 5,177,556 | 1/1993 | Rioux | 356/376 |

Primary Examiner—Richard A. Bertsch
Assistant Examiner—Howard R. Richman
Attorney, Agent, or Firm—Bruce L. Adams; Van C. Wilks

[57] ABSTRACT

A three-dimensional shape measurement system produces three-dimensional information of an object, such as an eye fundus, by directing light onto the object, receiving the light reflected from the object, photoelectrically converting the received light and processing the electric signal. The system includes laser beam control circuitry for focal point shifting in the direction of the optical axis, and a pair of detectors for detecting variation in the focal position of the light reflected from the object and deriving information respecting the shape of the object in the direction of the optical axis. Signal processing circuitry drives the laser beam control circuitry to produce a focused condition and adjusts the output signals of the detectors to a prescribed state.

20 Claims, 5 Drawing Sheets

THREE-DIMENSIONAL SHAPE MEASUREMENT SYSTEM

BACKGROUND OF THE INVENTION

1. Field of the Invention

This invention relates to a three-dimensional shape measurement system, and more particularly to a three-dimensional shape measurement system which produces three-dimensional information regarding a solid object under examination by receiving light reflected from the object, converting the received light into an electric signal, and processing the electric signal.

2. Description of the Prior Art

Numerous methods have been developed for optically measuring the three-dimensional shape of solid objects in a non-contact manner. Among the various applications of such optical three-dimensional shape measurement methods in the field of medicine, one that has drawn particular attention in recent years is a measurement apparatus for obtaining three-dimensional information regarding the fundus of the human eye.

Examination of the eye fundus provides important information not only for ophthalmologists but also in the field of internal medicine, where it is used in the diagnosis of hypertension, diabetes and other diseases. Photographing of the eye fundus with an eye fundus camera or the like has thus become a widely used medical procedure. Quantitative information regarding the pattern of irregularities (bumps and depressions) on the eye fundus is highly useful in the diagnosis of glaucoma and retinal detachment, as well as various types of edemas and tumors, and may be critical in preventing blindness. Because of this, attempts have been made to obtain three-dimensional image information regarding the eye fundus in addition to the ordinary two-dimensional image information.

One method of conducting such three-dimensional measurement involves projecting a specific grating pattern on the eye fundus, measuring the grating image shift by observation of the projected pattern from a direction differing from the direction of projection by a prescribed angle, and thus ascertaining the pattern of fundus depressions and the like. (See U.S. Pat. No. 4,423,931.)

Another method used for three-dimensional measurement of the eye fundus is based on the principle of stereoscopic photography. For example, a fundus camera is used to take two photographs at different angles from different entrance pupils and the resulting photographs are image-analyzed to ascertain the amount of fundus irregularity. Moreover, there has recently been developed a system that enables three-dimensional information to be obtained automatically by linking a TV camera with a computer, thus eliminating the need for photographic film. (See U.S. Pat. No. 4,715,703.)

However, in all of these prior art methods the imaging optical system of the eye is used nonaxially. As a result, the spatial resolution, accuracy and reproducibility of the three-dimensional measurement is poor and the processing of the signals is complex. Thus none of the methods is entirely satisfactory in terms of practical utility.

On the other hand, apparatuses that use the laser scanning method for in vivo observation of the eye fundus are becoming increasingly popular. (See Japanese Patent Public Disclosure No. Sho 62-117524, corresponding to U.S. Pat. No. 4,764,005, Japanese Patent Public Disclosure No. Sho 64-58237, corresponding to U.S. Pat. No. 4,854,692.) An attempt has been made to use this type of apparatus for measuring three-dimensional shape through a process that involves taking a plurality (e.g. 32) tomographic images of the eye fundus while progressively shifting confocal apertures located in front of a light detector and then reconstructing the fundus image. (See SPIE Proceedings, Vol. 1161, Sessions 7 and 8.) Since this laser scanning method uses the imaging optical system of the eye in a coaxial manner, the measurement accuracy is correspondingly high.

As a practical matter, however, the taking of a plurality of images requires the use of a large-capacity memory device, while the fact that the time needed for the measurement is not negligible means that the measurement accuracy is apt to be impaired by eye movement.

In response to this situation, the applicant therefore earlier proposed a highly innovative system for measuring the three-dimensional shape of objects that is based on a totally new principle. (See Japanese Patent Public Disclosure NO. Hei 1-113605, corresponding to U.S. Pat. No. 4,900,144 and Optics Communications, Vol. 74, 1989, pp. 165–170.) The principle of this invention is illustrated in simplified form in FIG. 4.

Figure 4:
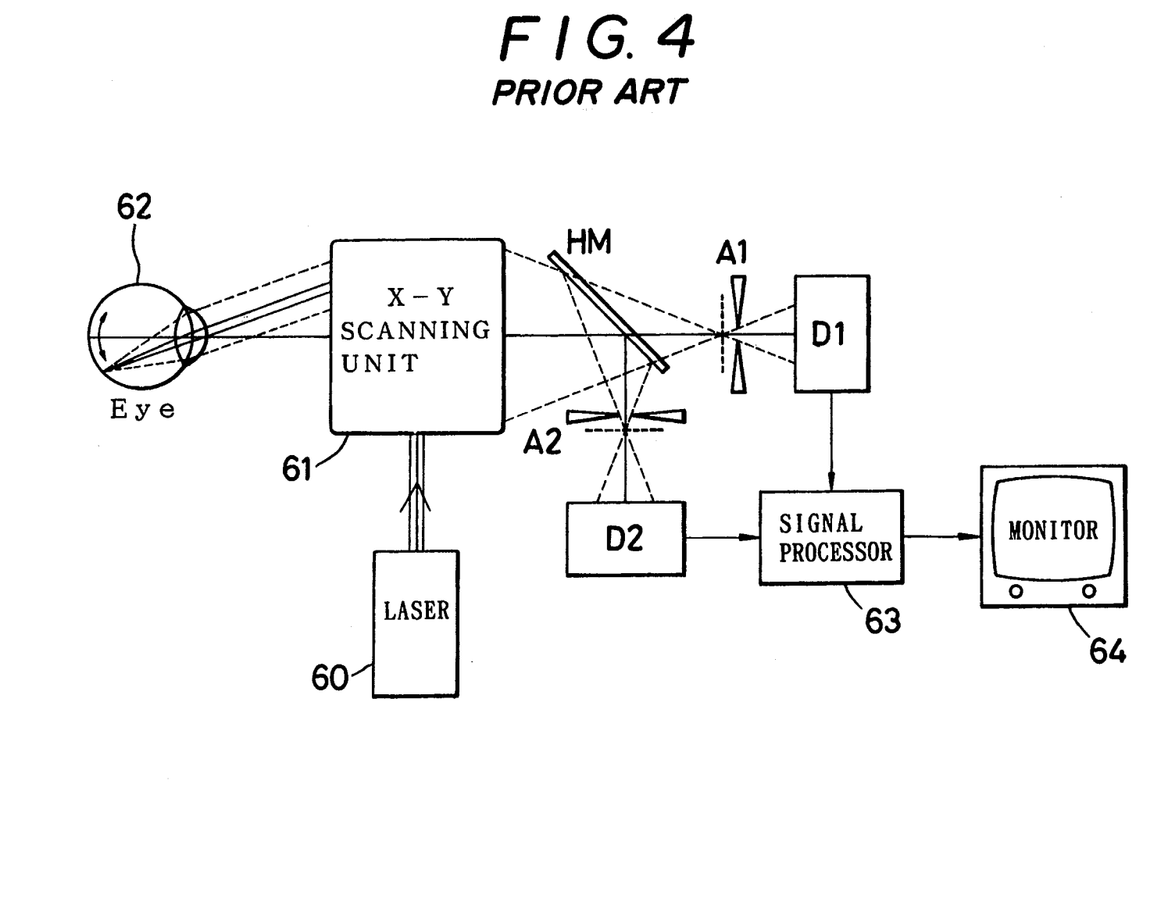
FIG. 4 is a schematic view of a prior art three-dimensional shape measurement system.

In FIG. 4, the laser beam from a laser beam source 60 is two-dimensionally deflected (scanned) by X-Y scanning unit 61 and the scanned beam is projected onto the fundus of an eye 62 under examination. The light reflected and scattered by the fundus passes back through the X-Y scanning unit 61, is split by a half mirror HM, and focused in the vicinity of two confocal apertures A1 and A2.

The apertures A1, A2 are disposed on the optical axes so as to sandwich the fundus focal plane. As a result, the increase and decrease in light intensity caused by irregularities (bumps and depressions) on the object (the eye fundus) are in reverse relationship between the two apertures.

The intensities of the light passing through the apertures A1 and A2 are detected by detectors D1 and D2, which produce output signals carrying irregularity information. Since the intensity of the output signals is also completely dependent on the reflectance of the object, the signals are sent to a signal processing unit 63 in which division processing is electrically conducted therebetween so as to cancel out the effect of the object reflectance and obtain information relating solely to the object irregularities. The result of the measurement or a measurement image is displayed on a TV monitor 64.

Figure 5:
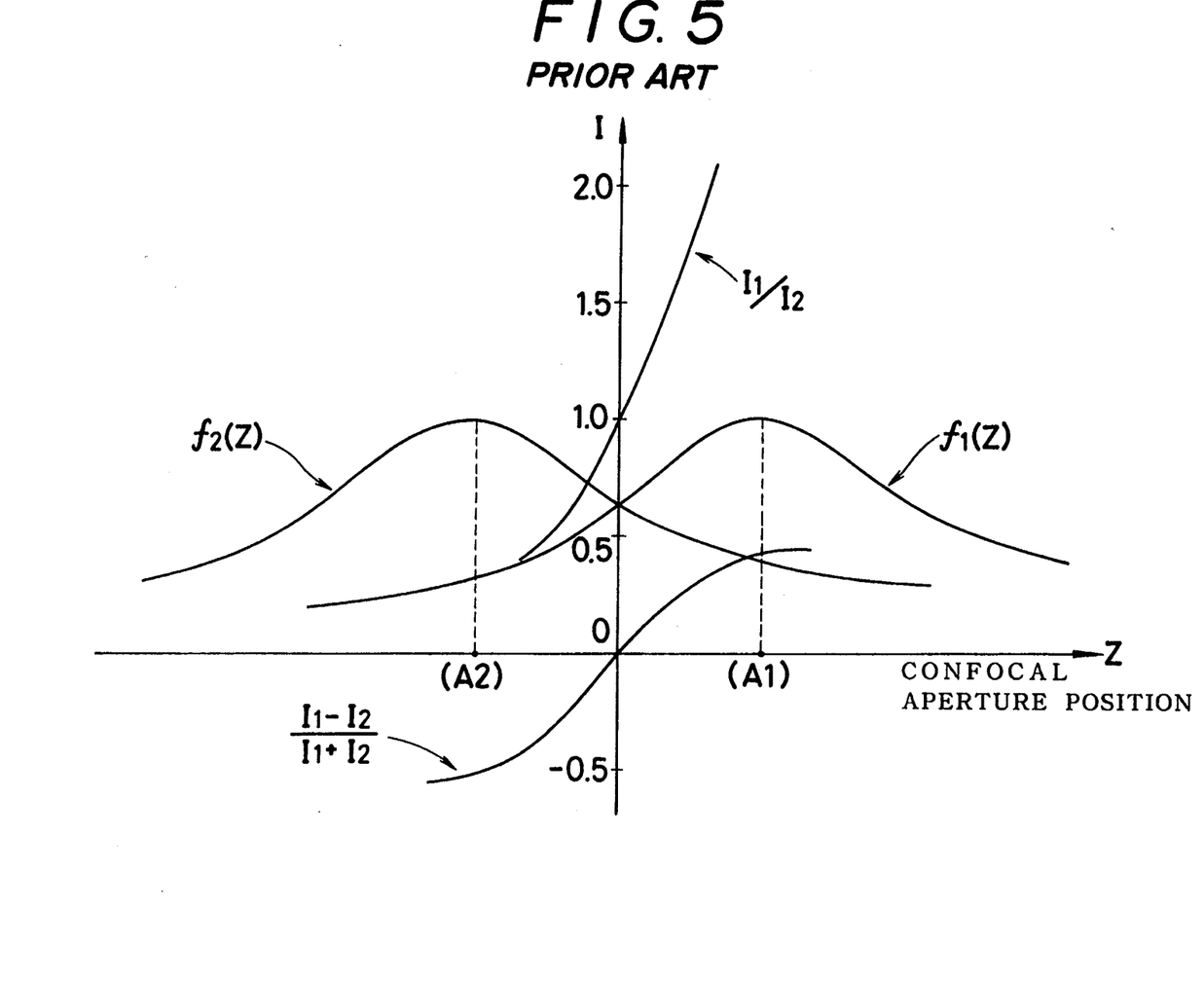
FIG. 5 is a graph for explaining the measurement principle of the prior art three-dimensional shape measurement system of FIG. 4.

FIG. 5 shows the intensity variation at the two detectors, in which the horizontal axis indicates the distance along the optical axis and (A1) and (A2) on the z axis represent the positions of the two apertures. Defining f1 (z) and f2 (z) as functions of the light intensity variation at the apertures, the signal intensities I1 and I2 at the detectors D1 and D2 can be expressed as follows $$I1 = f1(z) * Io(x, y) \tag{1}$$

$$I2 = f2(z) * Io(x, y) \tag{2}$$

where Io(x, y) is the variation in intensity of the light from the fundus and is dependent on position (x, y).

Therefore, by carrying out the following calculation involving division, it is possible to cancel out the effect of the reflectance dependent on position (x, y) and to obtain information of a form relating to the height or depth z.

$$I1/I2 = f1(z)/f2(z) \qquad (3)$$

or $$(I1-I2)/(I1+I2) = \hat{f1}(z) - \hat{f2}(z)\hat{U}/\hat{f1}(z) + \hat{f2}(z)\hat{U} \qquad (4)$$

Since applying this method for measurement of the three-dimensional shape of the eye fundus enables the imaging optical system of the eye to be used coaxially, it is able to provide high measurement accuracy. Moreover, it does not require a large-capacity memory, can be realized by simple signal processing in the signal processing unit 63 and enables the measurement of the object to be conducted in such an extremely short time as to provide substantially real-time observation of the three-dimensional shape.

However, the method does have a drawback in that when it is actually applied in a three-dimensional shape measurement system the effective range of the three-dimensional measurement in the z direction is limited to the region between (A1) and (A2) in FIG. 5. It is thus difficult to conduct accurate measurement when the focal plane of the object being measured falls outside the effective measurement range.

Moreover, where the measurement is carried out with respect to an eye fundus and has to be conducted in vivo, the measurement is complicated by the fact that the variation in refraction among the eyes of different patients causes variation in the focal plane. While it has been the practice to internally adjust the optical system in the instrument as required for examining patients with myopia, hyperopia and other refractive problems, an inexperienced operator is apt to have difficulty making the complex adjustments required so that erroneous measurements are likely to occur.

Another problem relates to the division processing required for implementing the method. High-speed, broad-band division circuits generally have a narrow input dynamic range and, as a result, the processing accuracy decreases when the intensity level of the detection signal falls outside this range.

The intensity level of the detection signal just before it is input to the division circuit is greatly dependent on the reflectance of the patient's eye fundus, the eye refractive condition, the transparency of the eye optical system and other factors. While it has been possible to adjust the detection signal level by changing the multiplication factor of the detectors themselves or that of the following circuitry, this is a complicated operation that may be a cause for measurement error if not conducted properly.

SUMMARY OF THE INVENTION

An object of the present invention is therefore to provide a three-dimensional shape measurement system which makes it possible to obtain accurate three-dimensional information regarding objects irrespective of object-to-object variation in reflectance or refractive condition or, in the case where the object is a human eye, in the transparency and the like of the eye optical system, without need for complex adjustment of the optical system or signal processing in the instrument.

In accordance with the present invention, there is provided a three-dimensional shape measurement system which produces three-dimensional information regarding an object under examination by irradiating the object with light, receiving light reflected from the object, converting the received light into an electric signal, and processing the electric signal. The system comprises a laser beam source for producing a laser beam, scanning means for two-dimensionally scanning the object with the laser beam, an optical system for directing the laser beam onto the object, laser beam control means for focal point shifting in the direction of the optical axis of the optical system which intersects the scanning directions of the scanning means, detection means for detecting variation in the focal position of the light reflected from the object and deriving from the detected variation information regarding the shape properties of the object in the direction of the optical axis of the optical system, first signal processing means for processing output signals of the detection means to eliminate the effect of the optical reflectance properties of the object, and second signal processing means for processing the output signals of the detection means to discriminate the condition of the focal position with respect to the object established by the laser beam control means so as to drive the laser beam control means to produce a focused condition or a third signal processing means for discriminating the intensity of the output signals of the detector means and adjusting the output signals of the detection means to a prescribed state.

In the aforesaid arrangement, the first signal processing means eliminates the effect of the optical reflectance of the object even in cases where the object is an in vivo eye fundus or the like exhibiting pronounced variation in optical reflectance and, as such, enables the extraction of information relating solely to the shape of the object.

Based on the detector output signal, the second signal processing means discriminates the focal condition of the optical system with respect to the object and automatically optimizes the focal condition of the laser beam in the optical system, thereby enabling the optical system to be controlled to within the focal range most appropriate for the measurement.

Moreover, the third signal processing means discriminates the electrical level of the detection signal and automatically maintains it at a constant intensity, thereby enabling an improvement in processing accuracy in the case of conducting high-speed, broad-band division processing.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENT

The invention will now be described in detail on the basis of the preferred embodiment illustrated in the drawings.

Figure 1:
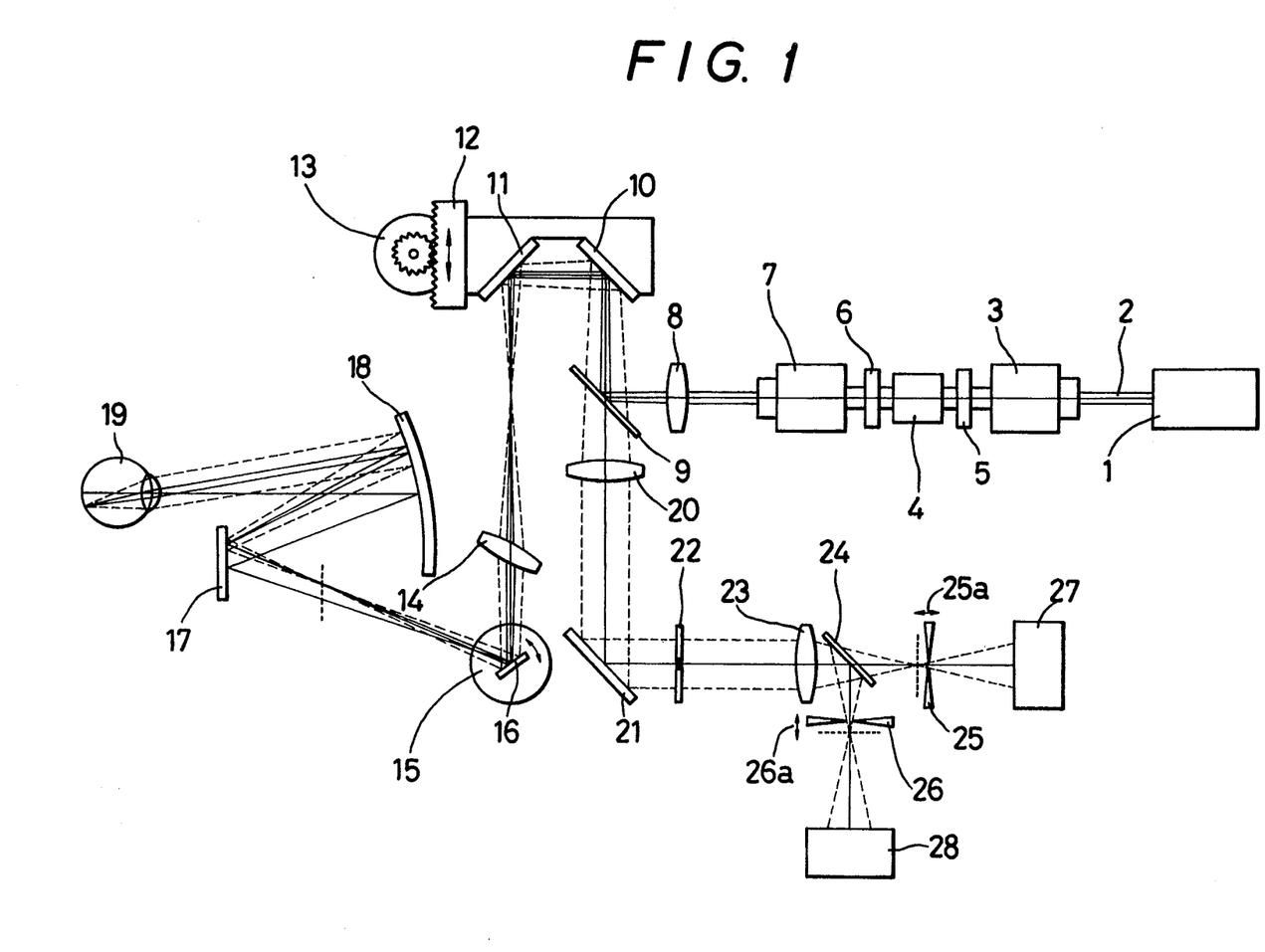
FIG. 1 is a schematic view of the optical system of a three-dimensional shape measurement system employing the present invention.

FIG. 1 shows an overall schematic view of the optical system of the three-dimensional shape measurement system according to the invention. A laser beam 2 emitted by a helium-neon (He—Ne), semiconductor or other such laser beam source 1 has its shape formed by passage through a lens 3 and then enters an acoustic-optical deflector (AOD) 4 by which it is scanningly deflected.

Prisms 5 and 6 are disposed before and after the AOD 4 to compensate for the light-wavelength dependency of the laser beam's angles of incidence and egression with respect to the AOD 4. These prisms are not absolutely necessary if a laser beam source which produces only monochromatic light is used.

The AOD 4 scanningly deflects the laser beam in one dimension at, for example, a frequency of 15.75 kHz, which corresponds to the horizontal scanning frequency used in ordinary TV systems. The laser beam scanned by the AOD passes through lenses 7 and 8, whereafter it is partially reflected and partially transmitted by a beam splitter 9.

The beam passing through the beam splitter 9 is received by a photodiode or the like (not shown) for monitoring the laser luminous energy.

The beam reflected by the beam splitter 9 is reflected and turned back by mirrors 10 and 11. The mirrors 10, 11 are mounted on a movable support 12 which is moved by a motor (stepping motor or the like) 13 for adjusting the focal point of the laser beam. The beam reflected by the mirrors 10, 11 passes through a lens 14 and falls incident on a mirror (galvanometer mirror) 16 mounted on a galvanometer 15.

For preventing the image quality from being degraded by surface-reflected light (stray light), it is preferable to dispose the lens 14 eccentrically with respect to the optical axis of the optical system, as shown in the drawing.

The portion between the lens 8 and the lens 14 is constituted as a telecentric optical system wherein the scanned laser beam is in a parallel state, and the mirrors 10, 11 are disposed in the optical system light path. It is therefore a characteristic of the system that the position at which the scanned laser beam forms an image on the galvanometer mirror 16, i.e. the center point about which the scanned beam swings, is maintained constant at all times notwithstanding changes in the focal position of the beam itself caused by movement of the mirrors 10 and 11.

The galvanometer mirror 16 scanningly deflects the laser beam at, for example, a frequency of 60 Hz, which corresponds to the vertical scanning frequency used in ordinary TV systems. Since the direction of the scanning by the galvanometer mirror 16 is perpendicular to that by the AOD 4, there is formed a two-dimensional laser raster corresponding to TV scanning lines. This raster is reflected by a mirror 17 and an objective mirror 18 to be projected through the center of the pupil of the eye 19 under examination and onto the eye fundus.

The light scattered by the eye fundus passes back along the optical path constituted by the elements 18, 17, 16, 14, 11 and 10 and then, after passing through the beam splitter 9, advances through a lens 20, is reflected by a mirror 21 and continues on through a glass plate 22. As the center of the glass plate 22 is blackened to make it opaque, it shuts out the reflected light from the cornea of the eye 19 under examination.

The beam of light passing through the glass plate is condensed by a lens 23, split by a half mirror 24, and focused in the vicinity of confocal apertures 25 and 26. The light beams passing through the two apertures are detected and photoelectrically converted by detectors 27 and 28 (photomultipliers, avalanche photodiodes or other such high-sensitivity detectors).

As was explained earlier, the two confocal apertures 25, 26 are located at positions on the optical axes offset slightly in opposite directions with respect to the points at which the images of the eye under examination are focused. This makes it possible to measure irregularities of the object (eye fundus) extending in the direction of the optical axis.

As shown in the drawing, the two apertures are offset for enabling the three-dimensional measurement. In this case, however, when the output signals of the two detectors are added together for ordinary image observation, the image contrast becomes somewhat inferior to that in the case where the apertures are perfectly aligned with the focal plane. Ideally, therefore, when this optical system is to be used for ordinary image observation, a fine adjustment mechanism should be provided for fine adjusting the positions of the two confocal apertures 25, 26 by shifting them slightly in the directions of the arrows 25a, 26a for bringing them into perfect alignment with the focal planes.

As another way for preventing contrast degradation during ordinary observation, it is possible for example to use a full mirror in place of the half mirror 24, position the aperture 26 in perfect alignment with the focal plane, and use only the output signal from the detector 28 (not use the output signal from the detector 27). Fine adjustment of the positions of the apertures in this way makes it possible to use the same optical system not only for conducting the three-dimensional measurement but also for observation of ordinary images (perfect confocal images) with minimal contrast degradation.

Figure 2:
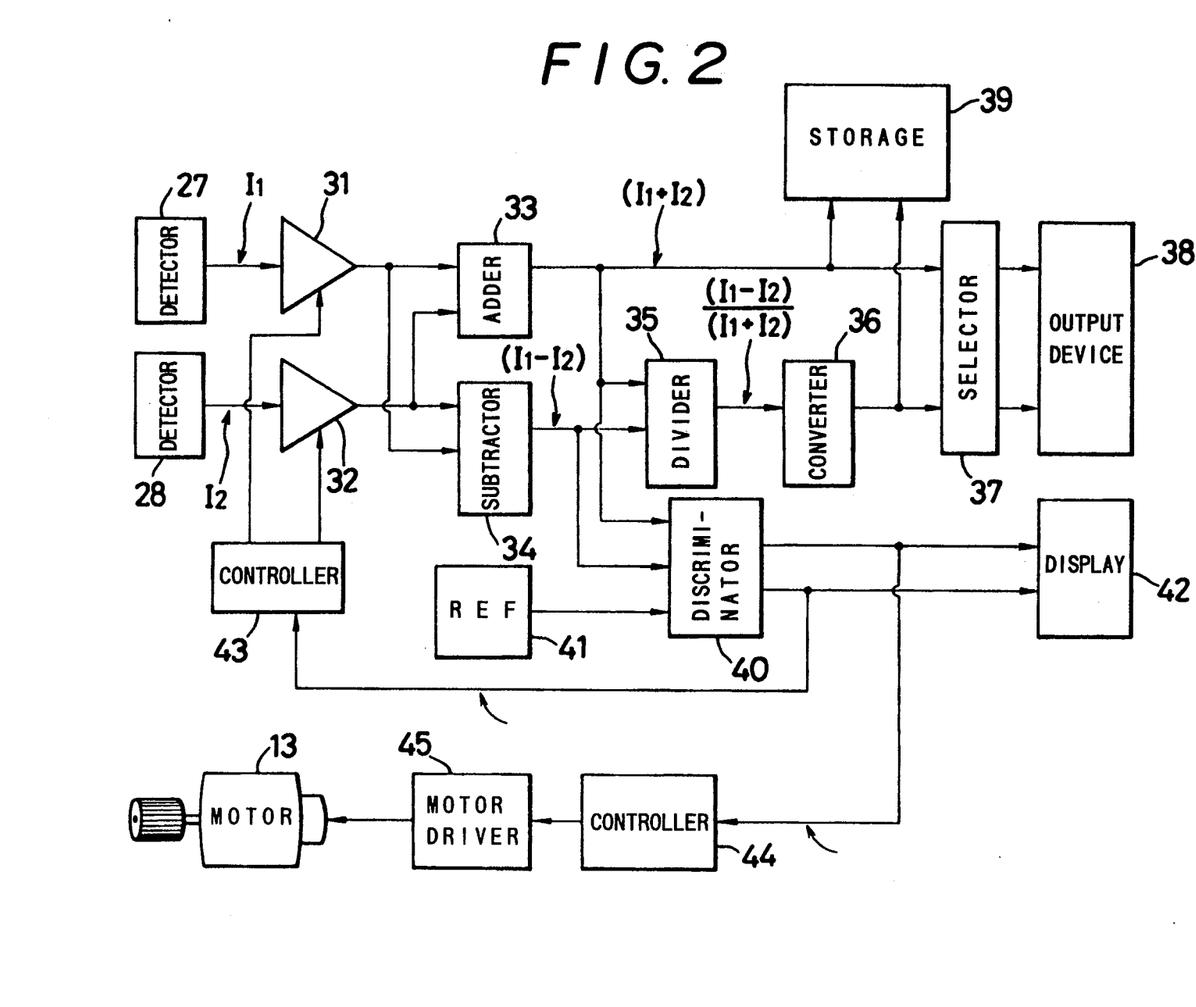
FIG. 2 is a block diagram of the signal processing system of a three-dimensional shape measurement system employing the present invention.

FIG. 2 is a block diagram of the electrical system for processing the received light signals in the three-dimensional shape measurement system according to the invention. Output signals I1 and I2 from the detectors 27, 28 (such as of the photomultiplier or avalanche photodiode type) are amplified in amplifiers 31 and 32 and then forwarded to an adder 33 and a subtracter 34. The sum and difference signals are sent to a divider 35 where they are subjected to division processing.

In the illustrated example, this means carrying out the calculation $(I1-I2)/(I1+I2)$ mentioned earlier (Eq. 4). The output signal from the divider is forwarded to a gradient converter 36 where it is corrected for nonlinearity, and then through a selector circuit 37 to a TV monitor or other such output device 38.

Although the sum and difference signals are divided in the aforesaid example, as was explained earlier the three-dimensional information can also be obtained in other ways, such as by direct division in the form of $I1/I2$ or by using the relationship $\log I1 - \log I2 = \log (I1/I2)$ (i.e., by using logarithmic conversion).

In the case where the selector circuit 37 selects the output signal ($I1+I2$) from the adder 33, an image of the object (fundus) for ordinary observation is displayed on the TV monitor. On the other hand, when it selects the division processed signal $(I1-I2)/(I1+I2)$, a three-dimensional image of the object (fundus) for detection of irregularities (bumps and depressions) is displayed.

In either case, the image information can if necessary be stored using a video tape recorder, magnetic disk drive, an optical disk drive or other such storage device 39.

The output signals from the adder 33 and the subtracter 34 are also sent to a discriminator 40 which uses them for checking the intensity levels of the signals and the focus condition of the optical system. The discriminator 40 has an internal comparator and logic circuit which discriminate the validity of the signals on the basis of reference voltages V1 and V2 from a reference voltage generator 41.

Figure 3:
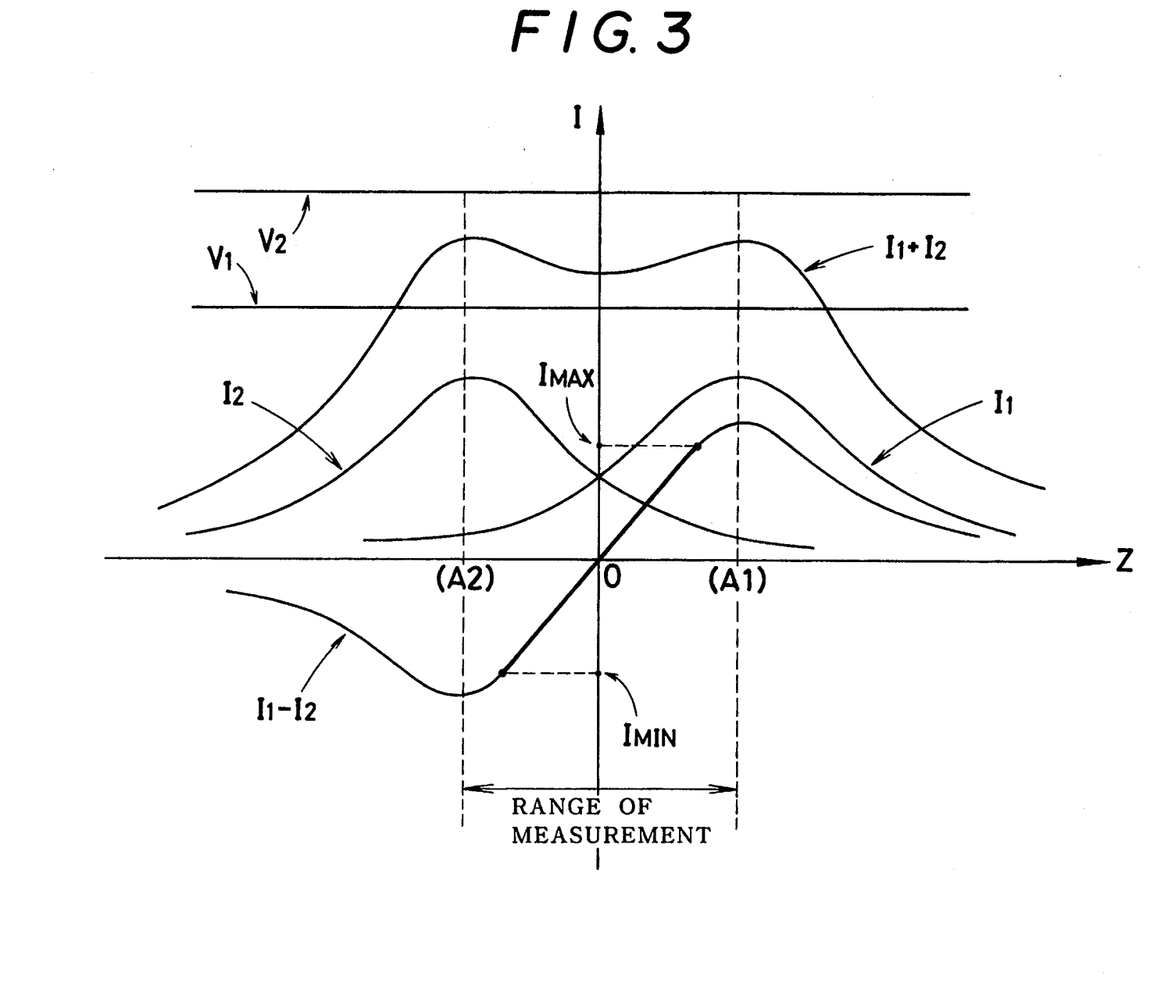
FIG. 3 is a graph for explaining the measurement principle of a three-dimensional shape measurement system employing the present invention.

FIG. 3 shows an example of the intensity levels of the two output signals from the detectors, before and after processing. As was explained earlier, each detector output signal I1,I2 exhibits an intensity curve which peaks at the position of one of the apertures A1 or A2 and the region between the peaks is the range over which measurement in the z direction is possible. If the focal plane of the object being measured should fall outside of this measurement range, measurement error is likely to occur.

Moreover, since dividers generally have a narrow dynamic range, it is important from the point of measurement accuracy for the level of the divider input signal, particularly the input level of the denominator of the division, to be within an appropriate range.

This appropriate range can be defined specifically as that:

with respect to $(I1-I2)$, I Max and I Min should satisfy the conditions of I Max$>0$, I Min$<0$ and absolute values of I Max and I Min approximately equal, and with respect to reference voltages V1 and V2 generated by the reference voltage generator 41, the relationship $V1<I1+I2<V2$ should be met.

Whether or not these conditions are met is detected by the discriminator 40.

If these discrimination conditions are met, this means that the focal plane of the optical system is within the measurement range in line with the three-dimensional measurement principle and that the denominator input level of the divider is also within the appropriate range.

Returning to FIG. 2, the result of the discrimination by the discriminator 40 is displayed on a display device 42, which may be an LED display or the like, and, in addition, feedback control is conducted by using the signal intensity discrimination signal to drive a controller or control circuit 43 for controlling the amplification factor of the two amplifiers 31, 32 so as to optimize the level of the signals.

On the other hand, the focus condition discrimination signal output by the discriminator 40 is forwarded through control circuit 44 and a drive circuit 45 to be used for controlling the motor 13 so as to control the optical system for ensuring that the focus condition is constantly maintained within the aforesaid appropriate range.

As explained in the foregoing, the present embodiment is provided with signal processing means which discriminates the focus condition of the optical system with respect to the object from the detector output signals and automatically maintains the focus condition of the laser beam in the optical system at optimum at all times, thus controlling the optical system so as to keep it within the focus range appropriate for the measurement. As a result, accurate three-dimensional measurement is possible irrespective of the type of object subjected to measurement.

In addition, since the present embodiment is provided with a signal processing means for discriminating the electrical level of the detector output signals and using the discriminated values for automatically maintaining the intensity condition of the signals in a constant state, the accuracy of the division processing is enhanced and, as a result, the accuracy and reproducibility of the three-dimensional measurement is upgraded.

While the present embodiment has been explained with respect to the case where the object subjected to measurement is an in vivo eye fundus, the invention is not limited this type of measurement and can also be applied to, for example, a scanning laser microscope or the like for use in examining the three-dimensional shape of microorganisms, cells, the fine wiring patterns of integrated circuits and the like.

Moreover, while the present embodiment uses an AOD and a galvanometer mirror as the scanning means, the invention is not particularly limited as regards the scanning method and it is alternatively possible to use any of various other scanning means such as a resonant type swinging mirror or a rotating polygonal mirror.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A three-dimensional shape measurement system for producing three-dimensional information of an object under examination, the system comprising:

a laser beam source for producing a laser beam;

scanning means for two-dimensionally scanning the object with the laser beam in two scanning directions;

an optical system for directing the laser beam along an optical axis onto the object so that the laser beam is reflected by the object as reflected light;

laser beam control means for focal point shifting in the direction of the optical axis of the optical system which intersects the scanning directions of the scanning means;

detection means for detecting a variation in focal position of the light reflected from the object and deriving, from the detected variation, information regarding shape properties of the object in a direction of the optical axis of the optical system and producing output signals representative of the shape properties of the object;

first signal processing means for processing output signals of the detection means to eliminate the effect of optical reflectance properties of the object; and second signal processing means for processing the output signals of the detection means to discriminate a condition of the focal position with respect to the object established by the laser beam control means so as to drive the laser beam control means to produce a focused condition.

2. A three-dimensional shape measurement system as set forth in claim 1, wherein the object under examination is an in vivo eye fundus and three-dimensional information is obtained regarding the eye fundus by irradiating it with light, receiving light reflected therefrom, converting the received light into an electric signal, and processing the electric signal.

3. A three-dimensional shape measurement system as set forth in claim 1, wherein the scanning means comprises a first deflector for deflecting the laser beam in a first direction at a first prescribed frequency and a second deflector for deflecting the laser beam in a direction perpendicular to the first direction at a second prescribed frequency lower than the first prescribed frequency.

4. A three-dimensional shape measurement system as set forth in claim 3, wherein the first deflector comprises an acoustic-optical deflector.

5. A three-dimensional shape measurement system as set forth in claim 3, wherein the second deflector comprises a galvanometer mirror.

6. A three-dimensional shape measurement system as set forth in claim 1, wherein the laser beam control means includes means for effecting focal point shifting by moving a reflecting mirror in a telecentric optical system.

7. A three-dimensional shape measurement system as set forth in claim 1, wherein the detection means includes two confocal apertures having respective focal distances and disposed so that their focal distances are offset in opposite directions with respect to point at which images of the object are focused.

8. A three-dimensional shape measurement system as set forth in claim 7, wherein at least one of the confocal apertures is adjustable to obtain an optically focused condition with respect to the object during observation of an ordinary image.

9. A three-dimensional shape measurement system as set forth in claim 1, wherein the first signal processing means includes a division circuit which calculates the quotient between the sum and the difference of the output signals of the detection means, thereby eliminating the effect of optical reflectance properties of the object.

10. A three-dimensional shape measurement system as set forth in claim 1, wherein the second signal processing means includes a discrimination circuit and, after calculating the sum and difference between the output signals of the detection means, causes the discrimination circuit to discriminate a focal condition of the optical system with respect to the object, whereafter it optimizes the focal condition of the laser beam by driving the laser beam control means.

11. A three-dimensional shape measurement system for producing three-dimensional information of an object under examination, the system comprising:
a laser beam source for producing a laser beam;
scanning means for two-dimensionally scanning the object with the laser beam in two scanning directions;
an optical system for directing the laser beam along an optical axis onto the object so that the laser beam is reflected by the object as reflected light;
laser beam control means for focal point shifting in the direction of the optical axis of the optical system which intersects the scanning directions of the scanning means;

detection means for detecting a variation in focal position of the light reflected from the object and deriving, from the detected variation, information regarding shape properties of the object in a direction of the optical axis of the optical system and producing output signals representative of the shape properties of the object;
one signal processing means for processing output signals of the detection means to eliminate the effect of optical reflectance properties of the object; and
another signal processing means for processing the output signals of the detection means to discriminate an intensity of the output signals of the detection means and adjusting the output signals of the detection means to a prescribed state.

12. A three-dimensional shape measurement system as set forth in claim 11, wherein the object under examination is an in vivo eye fundus and three-dimensional information is obtained regarding the eye fundus by irradiating it with light, receiving light reflected therefrom, converting the received light into an electric signal, and processing the electric signal.

13. A three-dimensional shape measurement system as set forth in claim 11, wherein the scanning means comprises a first deflector for deflecting the laser beam in a first direction at a first prescribed frequency and a second deflector for deflecting the laser beam in a direction perpendicular to the first direction at a second prescribed frequency lower than the first prescribed frequency.

14. A three-dimensional shape measurement system as set forth in claim 13, wherein the first deflector comprises an acoustic-optical deflector.

15. A three-dimensional shape measurement system as set forth in claim 13, wherein the second deflector comprises a galvanometer mirror.

16. A three-dimensional shape measurement system as set forth in claim 11, wherein the laser beam control means includes means for effecting focal point shifting by moving a reflecting mirror in a telecentric optical system.

17. A three-dimensional shape measurement system as set forth in claim 11, wherein the detection means includes two confocal apertures having respective focal distances and disposed so that their focal distances are offset in opposite directions with respect to points at which images of the object are focused.

18. A three-dimensional shape measurement system as set forth in claim 17, wherein at least one of the confocal apertures is adjustable to obtain an optically focused condition with respect to the object during observation of an ordinary image.

19. A three-dimensional shape measurement system as set forth in claim 11, wherein the one signal processing means includes a division circuit which calculates the quotient between the sum and the difference of the output signals of the detection means, thereby eliminating the effect of optical reflectance properties of the object.

20. A three-dimensional shape measurement system as set forth in claim 11, wherein the another signal processing means includes a discriminator for discriminating an intensity condition of the output signals of the detection means and producing a signal intensity discrimination signal, and a control circuit responsive to the signal intensity discrimination signal for maintaining an intensity level of the output signals of the detection means in a prescribed condition.

* * * * *